United States Patent
Busacca et al.

(10) Patent No.: US 7,186,827 B2
(45) Date of Patent: Mar. 6, 2007

(54) DIPEPTIDE SYNTHESIS

(75) Inventors: Carl Alan Busacca, Poughkeepsie, NY (US); Nizar Haddad, Danbury, CT (US); Suresh R. Kapadia, Danbury, CT (US); Lana Smith Keenan, Poughquag, NY (US); Jon Charles Lorenz, New Milford, CT (US); Chris Hugh Senanayake, Brookfield, CT (US); Xudong Wei, Ridgefield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 115 days.

(21) Appl. No.: 10/976,094

(22) Filed: Oct. 27, 2004

(65) Prior Publication Data

US 2005/0113572 A1    May 26, 2005

Related U.S. Application Data

(60) Provisional application No. 60/515,848, filed on Oct. 30, 2003.

(51) Int. Cl.
*C07D 403/12* (2006.01)
*C07D 413/12* (2006.01)

(52) U.S. Cl. ............... 540/481; 540/598; 540/601; 544/60; 544/111; 544/121; 544/129; 544/141; 544/365; 544/366; 546/189; 546/208

(58) Field of Classification Search ......... 544/129; 540/481
See application file for complete search history.

(56) References Cited

U.S. PATENT DOCUMENTS 6,420,364 B1    7/2002    Emmanuel 6,525,052 B2    2/2003    Bekkali
2004/0180886 A1*    9/2004    Hickey et al. ............ 514/230.5

OTHER PUBLICATIONS

Ang, Kiah How et al; Versatile Synthesis of Bicyclo[4.3.0]nonenes and Bicyclo[4.4.0]decenes by a Domino Heck-Diels-Alder Reaction; Tetrahedron vol. 52 No. 35 pp. 11503-11528; Elsevier Science Ltd. (1996).

Stammers, Timothy A. et al; Synthesis of Enantiomerically Pure Backbone Alkyl Substituted Peptide Nucleic Acids Utilizing the Et-DuPHOS-Rh+ Hydrogenation of Enamido Esters; Tetrahedron Letters vol. 40 (1999) pp. 3325-3328; Elsevier Science Ltd.

* cited by examiner

*Primary Examiner*—Joseph K. McKane
*Assistant Examiner*—Andrew B. Freistein
(74) *Attorney, Agent, or Firm*—Michael P. Morris; Anthony P. Bottino; Philip I. Datlow

(57) ABSTRACT

Disclosed are processes of making dipeptide compounds of formula(I) as further described in the detailed description section:

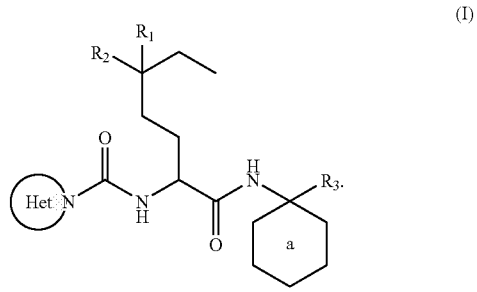

5 Claims, No Drawings

DIPEPTIDE SYNTHESIS

APPLICATION DATA

This application claims priority to U.S. provisional application Ser. No. 60/515,848 filed Oct. 30, 2003.

BACKGROUND OF THE INVENTION

1. Technical Field

This invention relates to synthetic processes for preparing dipeptide compounds possessing pharmacological activity, particularly as inhibitors of protease enzymes.

2. Background Information

Peptidyl nitrites have been reported as protease inhibitors. For example, both nitrites and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picornavirus protease. B. J. Gour-Salin (Can. J. Chem., 1991, 69, 1288) and T. C. Liang (Arch. Biochim. Biophys., 1987, 252, 626) described peptidyl nitrites as inhibitors of papain Examples of dipeptide nitrile-based cathepsin S inhibitors have been reported by Novartis application, WO 99/24460, 1999 and related U.S. Pat. No. 6,353,017. One of the generic structures is depicted below.

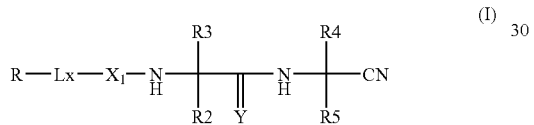

(I)

The processes provided therein provide for converting amides such as

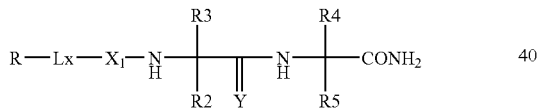

to the corresponding nitrites and several condensation reactions of intermediates to arrive at (I). The disadvantages of these methods are a linear sequence and deprotection/acylation reations after a chiral center is established which has the potential problems of racemization U.S. Pat. Nos. 6,525,052 and 6,420,364, U.S. provisional application Ser. No. 60/454,239 each commonly owned by the assignee of the present application, describe dipeptide nitrites bearing P1 heterocycles. One of the synthetic schemes shown in examples 2,3 and 5 discloses a process beginning with the preparation of intermediate 2-benzyloxy-carbonylamino-5,5-dimethyl-heptanoic acid for use in the synthesis of particular peptide nitrites disclosed therein.

EXAMPLES 2, 3 AND 5

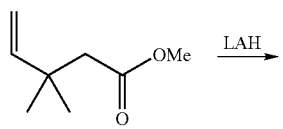

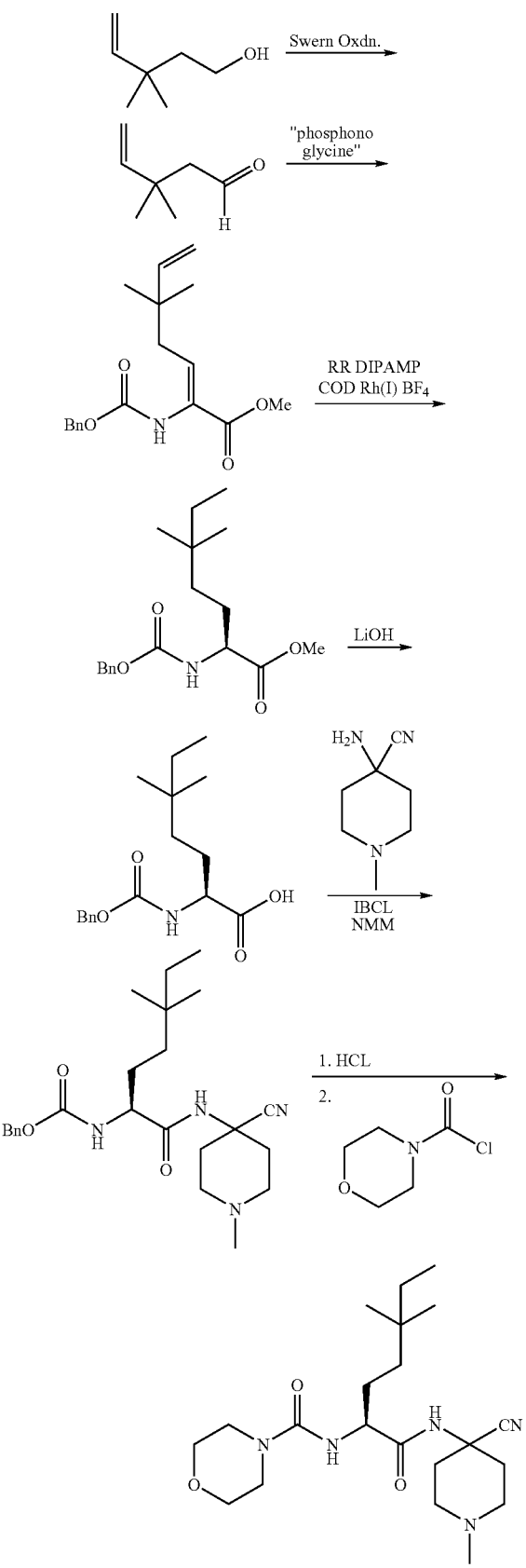

Compared to the aforementioned processes, the invention described herein provides an improved scalable and cost effective generalized process for preparing dipeptide compounds.

BRIEF SUMMARY OF THE INVENTION

It is therefore an object of the invention to provide a process of making dipeptide compounds of formula(I) as further described in the detailed description section:

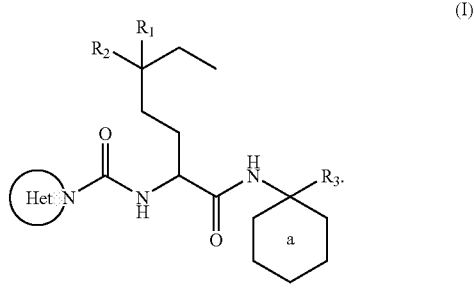

(I)

DETAILED DESCRIPTION OF THE INVENTION

The present invention has several advantages over similar known processes.

The key intermediate pentene aldehyde (IV) was synthesis by a novel palladium catalyzed tandem vinyl ether exchange—Claisen rearrangement process. This process is highly atomic and volumetric efficient. Known processes are only possible by using mercury salts as catalyst which is toxic. This process of the present invention avoided the use of reductant-oxidant found in the art, therefore it is more environmental friendly and cost effective.

Another advantage is that the urea-dehydroamino ester (VII) was efficiently synthesized by a "one-pot"—3 step sequence. This avoids isolation/purification work therefore saving solvent and labor work. The urea-dehydroamino ester (VII) could be purified by recrystallization which avoided the use of column chromatography for purification of dehydroamino esters in the art.

Although asymmetric hydrogenation of dehydroaminoester is known, the asymmetric hydrogenation of urea-substituted dehydroamino ester is not known in the art. The present inventors have successfully developed a highly enantioselective and high yielding hydrogenation process by using a newly developed catalyst TangPhos-Rh(COD)OTf.

In the broadest generic embodiment, there is provided a method of preparing dipeptide compounds of the formula (I):

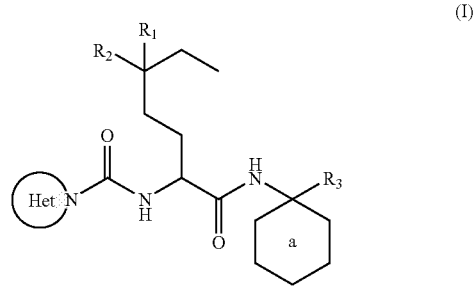

(I)

wherein:

Het is a monocyclic or bicyclic ring which is heterocyclic or a heteroaryl and contains at least the one nitrogen atom which is covalently attached to the carbonyl group as shown in the structure.

Preferred Het include azepanyl, azocanyl, pyrrolidinyl, piperidinyl, morpholinyl, thiomorpholinyl, piperazinyl, indolinyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl, benzoxazinyl and quinoxalinyl;

In a most preferred embodiment, Het is:

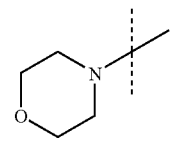

Ring a is azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydro-oxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydro-quinolinyl, decahydro-isoquinolinyl, 1,2,3,4-tetrahydro-quinolinyl, indolinyl, octahydro-quinolizinyl, dihydro-indolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl;

a $C_{6-10}$ bridged bicyclo wherein one or more carbon atoms are optionally replaced by a heteroatom chosen from N, O and S; or a $C_{4-7}$ cycloalkyl.

Preferred ring a include piperidinyl, pyrrolidinyl, azetidinyl and azepanyl; most preferred is piperidin-4-yl.

Each of ring a or Het is optionally substituted with one or more $R_4$ which is chosen from hydrogen or alkyl branched or straight chain alkyl, each carbon atom in the chain is optionally replaced with one to three heteroatoms chosen from O, S, and N—$R_5$ wherein $R_5$ is hydrogen or alkyl; and wherein $R_5$ is optionally further substituted by one or more alkoxy, amine, halogen, carbocycle, heteroaryl or heterocycle;

$R_1$ and $R_2$ are each independently alkyl, alkoxy, carbocycle, carbocycle(S(O)$_m$—, alkylS(O)$_m$— wherein m is 0, 1 or 2, heterocycle or heteroaryl. Preferred $R_1$ and $R_2$ is $C_{1-5}$ alkyl, most preferred is methyl.

$R_3$ is cyano, amino or —C(O)—Ar wherein Ar is a heterocycle, heteroaryl or carbocycle, preferably $R_3$ is cyano;

said process comprising:

a) reacting an allyl alcohol of the formula (II) with a vinyl ether of the formula (III) in the presence of a palladium catalyst and a ligand at a temperature range of 20° C. to 120° C., preferably about 70° C. A novel feature in this reaction step is that a vinyl ether exchange is combined with a Claisen rearrangement, the reaction occurs for about 7 h at about 100–200° C., preferably 120–145° C. Palladium catalysts include: Pd(OAc)$_2$, Pd(OCOCF$_3$)$_2$, PdCl$_2$, a preferred catalyst is Pd(O—C(O)—CH$_3$)$_2$; Ligands include: 1,10-phenathroline, 4,7-diphenyl-1,10-phenathroline, 2,2'-dipyridyl. A preferred ligand is 1,10-phenathroline.

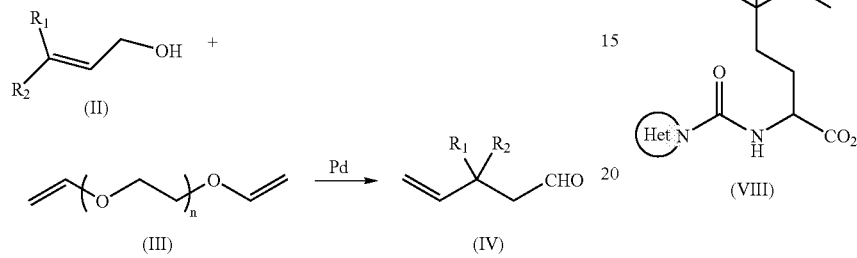

where n in formula (III) is 2, 3, 4 or 5 preferably 3.

b) In a one pot reaction, intermediate (V) is reduced and reacted with a nitrogen containing heterocycle (VI) where one of the nitrogen atoms bears an reactive acyl group such as —CO—X wherein X is a halogen atom, preferably chloro, and subsequently further reacted with the product (IV) above, to yield as product the novel intermediate (VII); (VII) is subsequently reduced by asymmetric catalytic hydrogenation such as H$_2$/Rh-(RRSS)-TangPhos under suitable conditions to provide ester (VIII). Intermediate (VIII) is subsequently hydrolyzed, preferably by a basic hydrolysis reaction, more preferably with aqueous LiOH to produce the acid (IX):

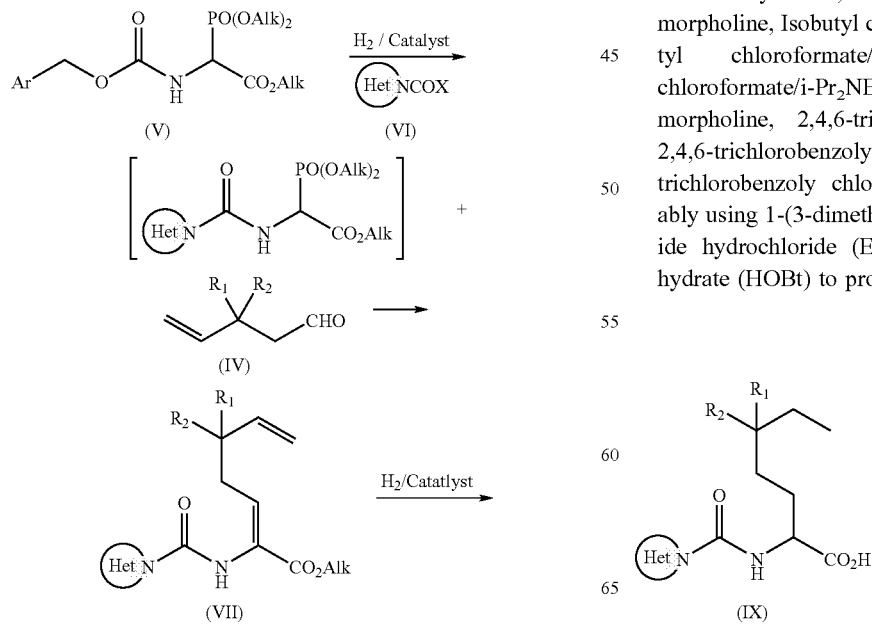

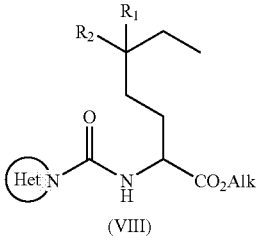

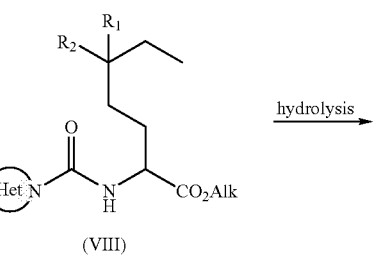

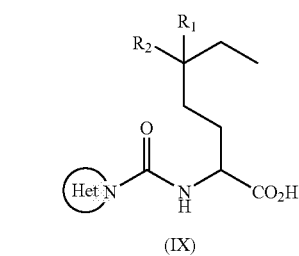

c) The intermediate (IX) produced above is subsequently reacted with an amine intermediate bearing ring a under suitable coupling conditions such as EDC/HOBt, N,N'-Dicyclohexylcarbodiimide (DCC), N,N'-diisopropylcarbodiimide (DIC), O-(1H-Benzotriazol-1-yl)-N,N,N'N'-tetramethyl-uronium hexafluorophosphate, Trimethylacetyl chloride/i-Pr$_2$NEt, Trimethylacetyl chloride/Triethylamine, Trimethylacetyl chloride/N-methylmorpholine, Isobutyl chloroformate/triethylamine, Isobutyl chloroformate/N-methylmorpholine, Isobutyl chloroformate/i-Pr$_2$NEt, Ethylchloroformate/N-methylmorpholine, 2,4,6-trichlorobenzoly chloride/i-Pr$_2$NEt, 2,4,6-trichlorobenzoly chloride/triethylamine, 2,4,6-trichlorobenzoly chloride/Nomethylmorpholine, preferably using 1-(3-dimethylaminopropyl)-3-ethylcarbodiimide hydrochloride (EDC) and 1-hydroxybenzotriazole hydrate (HOBt) to produce (I):

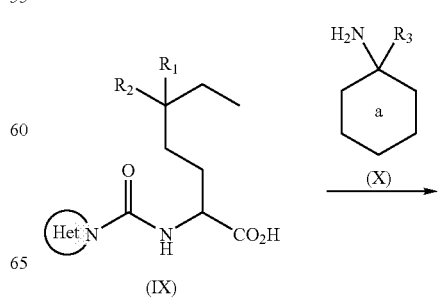

-continued

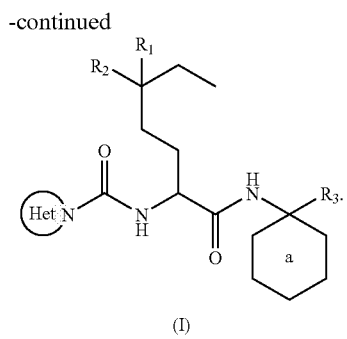

(I)

Unless otherwise noted, any compounds produced by the methods of this invention which contain one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations.

In preferred embodiments of the invention, in product compounds the P2 chiral carbon is the (S) enantiomer which possesses a natural amino acid configuration. Some of the compounds of the invention can exist in more than one tautomeric form. The invention includes producing all such tautomers.

It shall be understood by one of ordinary skill in the art that all compounds produced by the methods disclosed herein are those which are chemically stable.

In order that the invention herein described may be more fully understood, the following detailed description is set forth. As used herein, the following abbreviations are used:
BOC or t-BOC is tertiary-butoxycarbonyl;
t-Bu is tertiary-butyl;
DMF is dimethylformamide;
EtOAc is ethyl acetate;
OAc is acetate;
THF is tetrahydrofuran;
NMM is 4-methyl morpholine
$CH_2Cl_2$ is dichloromethane;
$MgSO_4$ is magnesium sulfate;
$Na_2SO_4$ is sodium sulfate;
Ar is argon;
EDC is 1-(3-dimethylaminopropyl)-3-ethylcarbodiimide hydrochloride and HOBT is 1-hydroxybenzotriazole;
DBU is 1,8-diazabicyclo[5.4.0]undec-7-ene;
MTBE is tert-butyl methyl ether.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

Carbocycle refers to "aryl" being aromatic ot partially saturated, or a nonaromatic cycloalkyl.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated.

The term "aryl" refers to phenyl and naphthyl.

The term "halogen" refers to a halogen radical selected from fluoro, chloro, bromo or iodo.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Unless otherwise defined, examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, The term "heterocycle" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Unless otherwise defined, examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C=O).

Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

The term "amine" shall be understood to mean an —$NH_2$ group wherein each hydrogen atom may be replaced by alkyl, carbocycle, carbocyclealkyl, heteroaryl, heteroarylalkyl, heterocycle, heterocyclealkyl such that the amine nitrogen may be mono- or di- substituted by said groups.

As used herein above and throughout this application, "nitrogen" and "sulfur" include any oxidized form of nitrogen and sulfur and the quaternized form of any basic nitrogen.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art. Further reference in this regard may be made to U.S. Pat. Nos. 6,525,052 and 6,420,364, U.S. provisional application Ser. No. 60/454,239.

All journal and patent references cited in this application are incorporated herein by reference in their entirety.

EXAMPLES

Synthesis of 3,3-Dimethylpent-4-enal by Sequential Vinylether Formation and Claisen Rearrangement

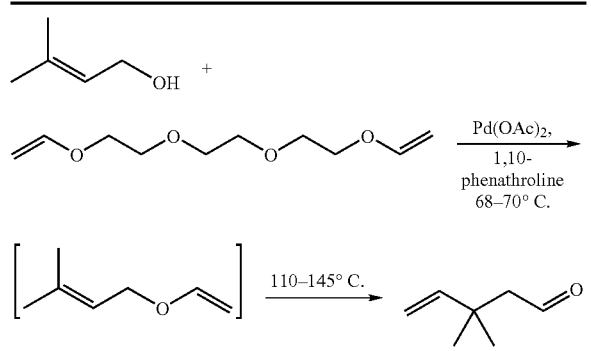

| Compound | MW | Mass | Mol | eq |
|---|---|---|---|---|
| 3-methyl-2-butenol | 86 | 1.72 Kg | 20 mol | 1.0 |
| Triethyleneglycol divinyl ether | 202 | 6.06 Kg | 30 mol | 1.5 |
| Pd(OAc)$_2$ | 224 | 22.4 g | 0.1 mol | 0.005 |
| 1,10-phenathroline | 180 | 18.0 g | 0.1 mol | 0.005 |
| 1,4-Butynediol | 43 | 12.0 g | 0.28 mol | 0.014 |

Pd(OAc)$_2$ (22.4 g, 0.1 mol) and 1,10-phenathroline (18.0 g, 0.1 mol) were added to a 12 L 3-neck flask. Triethyleneglycol divinyl ether (6.06 kg, 6 L, 30 mol) was added, and the mixture was stirred at room temperature for 20 minutes while a lemon yellow suspension was formed. 3-Methyl-2-butenol (1.72 kg, 2 L, 20 mol) was added, and the reaction mixture was heated gently to 68–70° C. The reaction became a clear yellow solution at this point. After stirring for 5–7 h, NMR showed that about 80% of 3-methyl-2-butenol had been converted to its vinyl ether. 1,4-Butynediol (12 g, 0.28 mol) was added, and the reaction mixture was then heated up to 110–120° C. The temperature was raised gradually to 145° C. within ca. 1 h in order to maintain the reflux and then kept at this temperature for 5–10 h until $^1$H-NMR showed the rearrangement finished. The reaction mixture was cooled to ca. 120° C. and distilled under vacuum. The fraction at ca. 90° C./300 mm Hg was collected. 1.34 kg of the desired product was obtained (60% yield) as colorless liquid.

"One pot" Synthesis of Dehydrourea Ester (Steps 2–4):

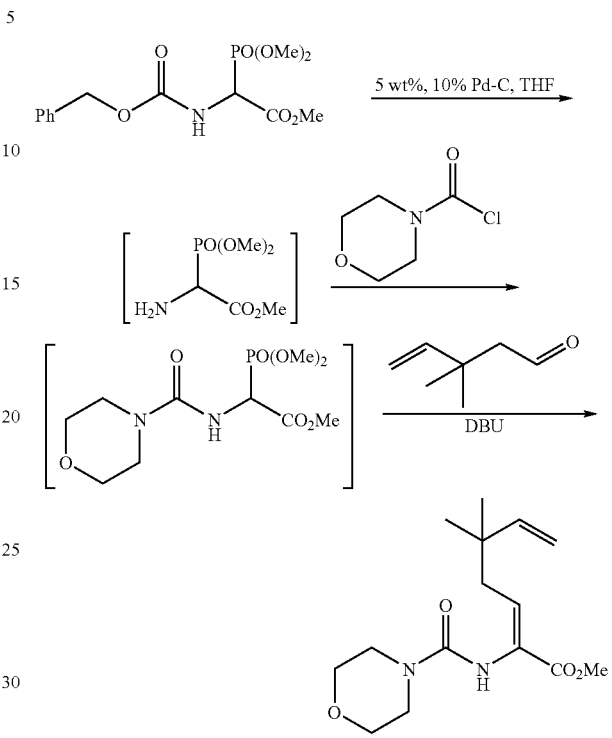

Hydrogenation of N-(benzyloxy carbonyl)-α-Phosphonoglycine Trimethyl Ester

A dry 20 L autoclave was pressure tested at 100 psi with N$_2$ then vented, and placed under vacuum. A solution of Cbz-α-phosphono glycine trimethylester (3.0 kg 9.06 mol) in THF (12 L) was transferred into the autoclave using residual vacuum. The cooling water for the agitator was turned on, the batch was agitated at 500 to 700 rpm, and the autoclave was purged with N$_2$ for 10–15 min, then placed under a slight vacuum. A slurry of Degussa type E101 NE/W ~50% H$_2$O wet Pd/C (600 g, 10 wt %) in a minimal amount of THF was transferred to the reactor using residual vacuum. The reactor was sealed, purged with nitrogen, pressurized to 10 psi with hydrogen and vented twice. The reactor was filled to 100 psi using a line with a check valve, and the line was left open to maintain the internal pressure at 100 psi. After 4 h the H$_2$ was slowly vented, a sample was taken for HPLC to confirm the reaction contained less than 2% starting material. Using vacuum the reaction was transferred to a filter funnel containing MgSO$_4$ (1 kg) to remove the Pd/C and H$_2$O. The pad was rinsed with THF and the filtrated taken directly to the next step.

Note: Do not allow the pad to become dry during the filtration, fire hazard.

Note: The amino phosphono ester generated in this reaction is extremely unstable when concentrated and can decompose explosively.

Urea Formation

The above amine-containing solution was transferred to a 50 L flask fitted with a mechanical stirrer, thermocouple and nitrogen inlet. The 4-morpholine carbonyl chloride (1.25 L, 10.9 mol) and N-methyl morpholine (1.64 L, 14.9 mol) were added at 17° C., there was a mild delayed exotherm of a few degrees, and the reaction was left overnight. The reaction was followed by $^{31}$P NMR, or LCMS. When the reaction was complete it was used without work-up or purification in the next step.

Horner Emmons Wadsworth Reaction

The slurry of urea phosphono ester in THF was cooled to about 10° C. and 3,3-dimethyl-4-pentenal (1.35 kg, 83% pure, 1.0 mol) was added, with a THF rinse (2 L). The DBU (2.9 kg, 19 mol) was charged to an addition funnel and added to the reaction dropwise over 3.5 h while maintaining the internal temperature of the reaction between 6–17° C. After the addition was complete the reaction was allowed to slowly warm to room temperature and followed by LCMS. When the phosphonate had been consumed by LCMS the slurry was cooled in an ice bath to about 4° C. and 4 M HCl (12 L) was slowly dripped into the reaction over 2.5–3.5 h, while keeping the reaction temperature below 20° C. The layers were then separated, the aqueous layer was extracted with EtOAc (2×8 L), the organic layers were combined, washed with 1 M HCl (6 L) and concentrated by distillation to give the crude product as a slurry/solid.

Crystallization

The two batches were combined, EtOAc (4 L) was added, then distilled off under hose vacuum below 50° C. to remove most of the THF. The crude material was mixed with EtOAc (1.8 L) and heptane (3.8 L) and heated in a water bath to 70° C., a solution formed at about 66° C. The solution's temperature was slowly lowered to ambient over several h then left to stir at ambient temperature overnight. The solid was collected by vacuum filtration, and the flask was rinsed with the mother liquors. The off white solid was dried in a vacuum oven below 40° C. with a nitrogen purge to yield 3.7 kg with an E/Z ration of 1/126.

The product was further purified by slurrying the dehydro urea ester (3.6 kg) in a 22 L flask with H$_2$O (9 L) for 2.5 h, collecting the white solid by vacuum filtration, and drying in a vacuum oven below 40° C. to give 2.98 kg of the desired product as a fluffy white solid.

Synthesis of Substituted Chiral Amino Ester by Asymmetric Hydrogenation

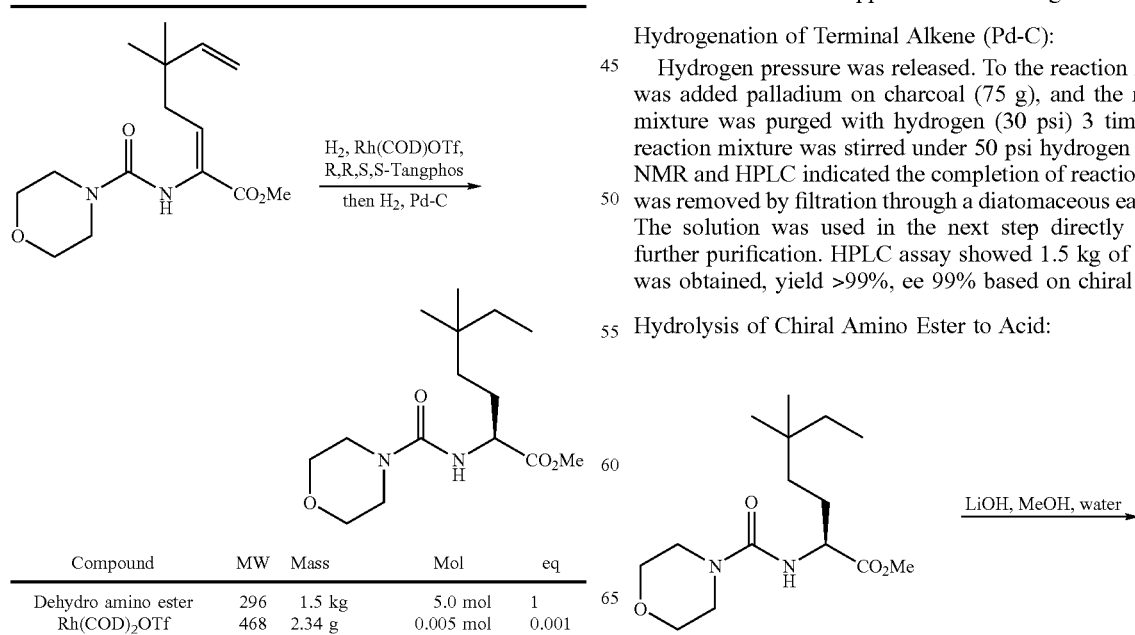

| Compound | MW | Mass | Mol | eq |
|---|---|---|---|---|
| Dehydro amino ester | 296 | 1.5 kg | 5.0 mol | 1 |
| Rh(COD)$_2$OTf | 468 | 2.34 g | 0.005 mol | 0.001 |
| (RRSS)-TangPhos | 286 | 1.57 g | 0.0055 mol | 0.0011 |
| MeOH | | 6 L | | solvent |
| Pd-C (10%, 50% wet) | | 75 g | | (1:20) |

Preparation of Chiral Catalyst:

Rh(COD)$_2$OTf and ligand were mixed in methanol (500 ml) under Ar. The solution was stirred at ambient temperature for 30 min. Hydrogen was bubbled through it for another 15 min.

Asymmetric Hydrogenation:

The dehydroaminoester in 5.5 L methanol was added to an autoclave. The solution was purged with hydrogen at 30 psi 4 times. The solution of chiral catalyst was added with a canula, and the reaction mixture was stirred under 50 psi hydrogen for 10 h at ambient temperature. NMR and HPLC both indicated the disappearance of starting material.

Hydrogenation of Terminal Alkene (Pd-C):

Hydrogen pressure was released. To the reaction mixture was added palladium on charcoal (75 g), and the reaction mixture was purged with hydrogen (30 psi) 3 times. The reaction mixture was stirred under 50 psi hydrogen for 3 h. NMR and HPLC indicated the completion of reaction. Pd-C was removed by filtration through a diatomaceous earth pad. The solution was used in the next step directly without further purification. HPLC assay showed 1.5 kg of product was obtained, yield >99%, ee 99% based on chiral HPLC.

Hydrolysis of Chiral Amino Ester to Acid:

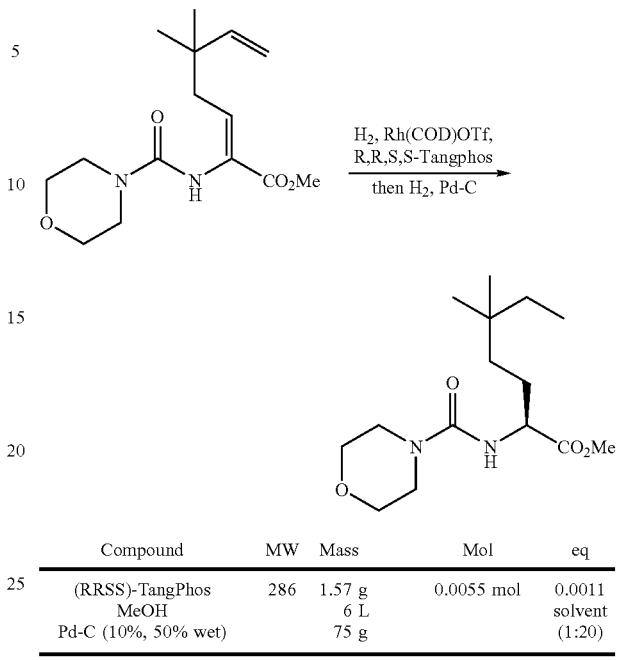

-continued

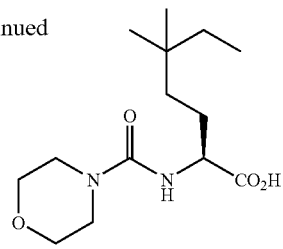

To a 22 L three neck flask fitted with a mechanical stirrer and nitrogen inlet was added the ester (1.40 kg, 4.66 mole). Methanol (4.20 L) and THF (4.20 L) were charged into the flask and the contents were stirred until a clear solution was obtained. A solution of lithium hydroxide (215.10 g, 5.13 mole, 1.1 eq) in 4.20 L of water was added slowly to the flask. The reaction temperature was maintained below 30° C. using a cold water bath. At the end of the addition the cold bath was removed and the reaction mixture was stirred at 22±2° C. for 2 h. The pH of the reaction mixture was adjusted to about 5–6 by the addition of 2N HCl (1.40 L) keeping the internal temperature between 15–20° C. The mixture was subjected to distillation under reduced pressure to remove volatile solvents (MeOH and THF). The residue was adjusted to pH ~3 with 2N HCl (1.82 L) and extracted with MTBE (2×4.66 L). The combined organic phase was washed with saturated brine (2.30 L). The organic layer containing the acid (about 11.8 L) was concentrated by distillation of MTBE to a minimum stirrable volume. MTBE (9.30 L) was added and the resulting mixture distilled under reduced pressure. Anhydrous THF (9.30 L) was then added to the residue and distilled under reduced pressure to a minimum stirrable volume. Anhydrous THF (7.0 L) was added to the residue. The solution was assayed by HPLC and stored it in a cool dry place under nitrogen.

Procedure for Amide Coupling:

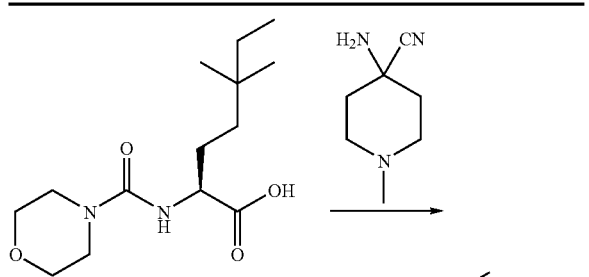

| Material | MW | eq. | Mol | Amount |
|---|---|---|---|---|
| Acid (ee = 99.4%) | 286.37 | 1 | 4.19 | 1.20 Kg |
| HOBT.H$_2$O | 153.14 | 1.32 | 5.53 | 0.847 Kg |

-continued

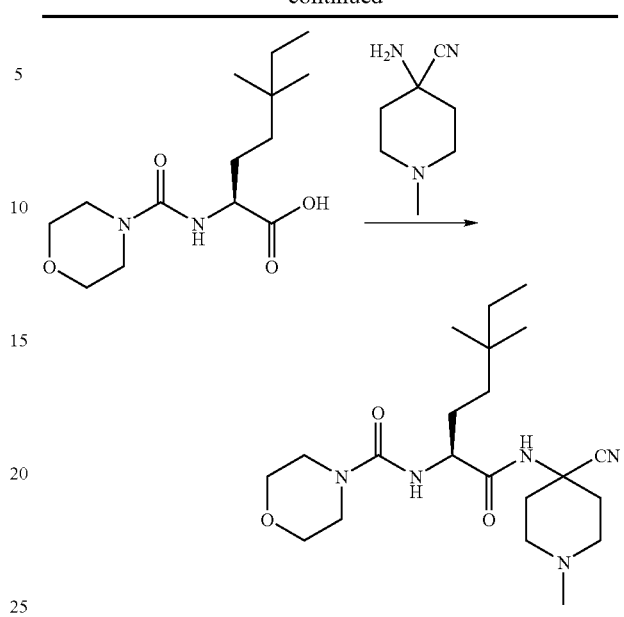

| Material | MW | eq. | Mol | Amount |
|---|---|---|---|---|
| EDC | 191.7 | 1.37 | 5.76 | 1.105 Kg |
| Aminonitrile | 139.2 | 1.15 | 4.82 | 0.671 Kg |
| THF | | | | 2.88 L |
| DMF | | | | 2.88 L |

To a solution of acid (1.20 kg, 4.19 mol) in THF (2.8 L) was added anhydrous DMF (2.88 L) and HOBT (0.706 kg, 4.61 mol). EDC (0.884 kg, 4.61 mol) was added in several portions keeping temperature between 15 and 17° C. After stirring for 1 h, the aminonitrile (0.671 kg, 4.82 mol) was added over 45 min (T<20° C.) and the reaction mixture was stirred for 3 h. At this time remaining HOBT (0.141 kg) and EDC (0.221 kg) were added and stirred for 16 h at ambient temperature. The reaction mixture was filtered to remove particulate matter and quenched by pouring into 7% sodium bicarbonate solution (29 L). The mixture was stirred for 4 h at ambient temperature. The product was filtered and washed with water (3×5 L) and dried under N$_2$. Isolated yield: 1.32 kg (77.3%), ee=100%, purity 97.55% by HPLC.

What is claimed is:

1. A process of preparing a compound of the formula (I):

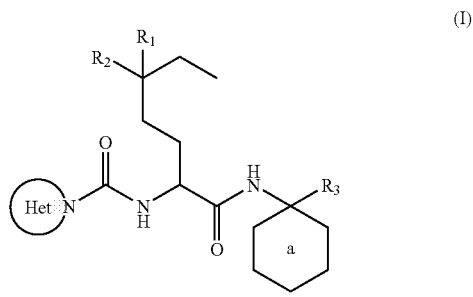

(I)

wherein:
  Het is a monocyclic ring which is heterocyclic and contains at least the one nitrogen atom which is covalently attached to the carbonyl group;
  Ring a is: piperidinyl, hexahydropyrimidinyl, hexahydropyridazinyl, piperazinyl, 1,2-thiazinanyl-1,1-dioxide, 1,2,6-thiadiazinanyl-1,1-dioxide, morpholinyl, or thiomorpholinyl;
  each of ring a or Het is optionally substituted with one or more $R_4$ which is chosen from hydrogen and branched or straight chain alkyl, each carbon atom in the alkyl chain is optionally replaced with one to three heteroatoms chosen from O, S, and N—$R_5$ wherein $R_5$ is hydrogen or alkyl; and wherein $R_5$ is optionally further substituted by one or more alkoxy, amine, halogen, carbocycle, heteroaryl or heterocycle;
  $R_1$ and $R_2$ are each independently alkyl, alkoxy, carbocycle, carbocycleS(O)$_m$—, alkylS(O)$_m$— wherein m is 0, 1 or 2;
  $R_3$ is cyano or amino;
  said process comprising:
  a) reacting an allyl alcohol of the formula (II) with a vinyl ether of the formula (III) in the presence of a palladium catalyst and a ligand chosen from 1, 10-phenathroline, 4, 7-diphenyl-1, 10-phenathroline and 2,2'-dipyridyl at a temperature range of 20° C to 120° C., continuing the reaction for about 7 h at about 100–200° C.;

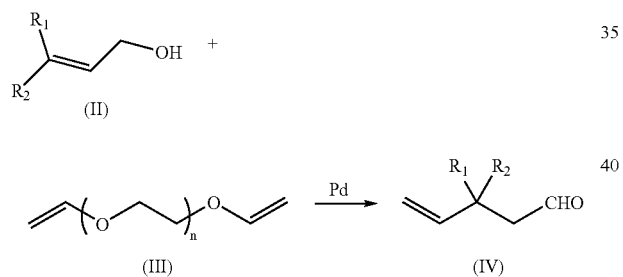

where n in formula (III) is 2, 3, 4 or 5;
  b) in a one pot reaction, reducing an intermediate (V) and reacting (V) with a nitrogen containing heterocycle (VI) where one of the nitrogen atoms bears a reactive acyl group: —CO—X wherein X is a halogen atom, and subsequently further reacting with the product (IV) above, to yield as product intermediate (VII);
  subsequently reducing (VII) by asymmetric catalytic hydrogenation to provide ester (VIII);
  hydrolyzing intermediate (VIII) to produce the acid (IX):

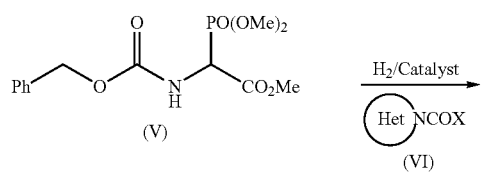

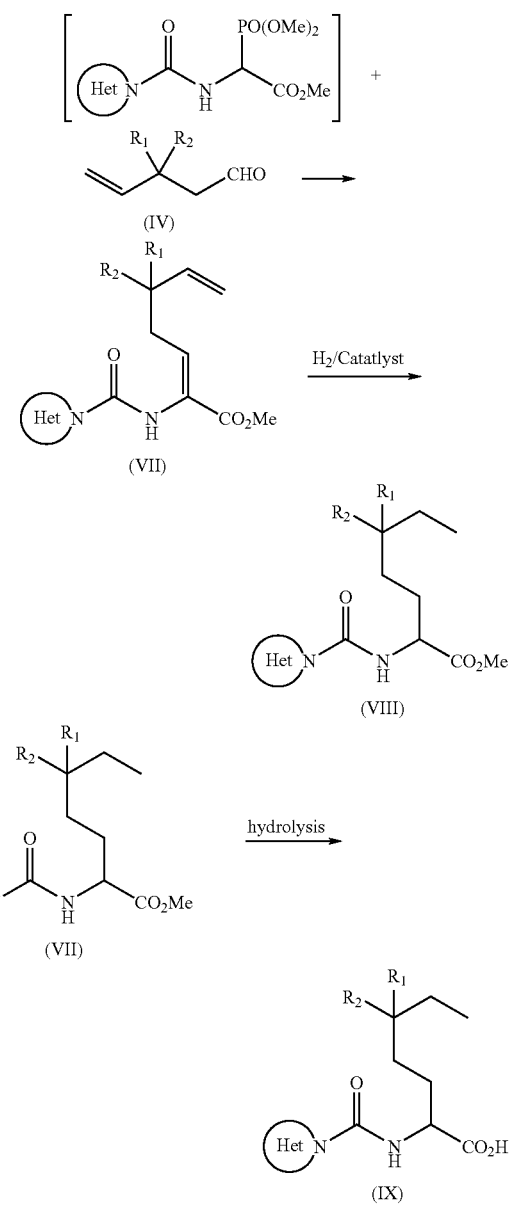

c) reacting the intermediate (IX) produced above with an amine intermediate bearing ring a under coupling conditions to produce (I):

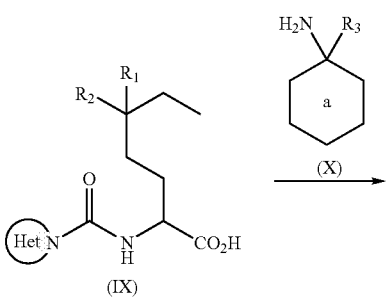

-continued

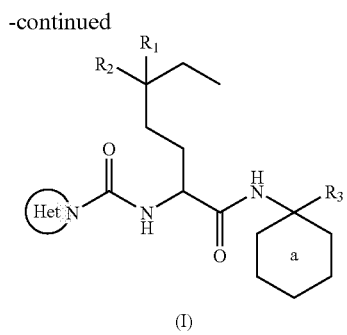

and subsequently isolating the product (I).

2. The process according to claim 1 wherein:
Het is chosen from azepanyl, azocanyl, pyrrolidinyl, piperidinyl, morpholinyl, thiomorpholinyl and piperazinyl;
ring a is piperidinyl;
$R_1$ and $R_2$ are $C_{1-5}$ alkyl; and
$R_3$ is cyano.

3. The process according to claim 2 wherein Het is:

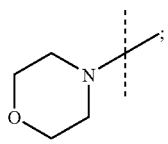

ring a is piperidin-4-yl; and
$R_1$ and $R_2$ are methyl.

4. The process according to any one of claims 1–3 wherein:
step a):
the reaction of the allyl alcohol of the formula (II) with a vinyl ether of the formula (III) in the presence of a palladium catalyst and a ligand is at a temperature of about 70° C., the continuing reaction is for about 7 h at about 120–145° C.;
wherein the palladium catalyst is: Pd(O—C(O)—CH$_3$)CH$_2$, Pd(OCOCF$_3$)$_2$ or PdCl$_2$;
and wherein n in formula (III) is 3;
step b):
X is chloro;
(VII) is subsequently reduced by asymmetric catalytic hydrogenation using H$_2$/Rh-(RRSS)-TangPhos to provide ester (VIII);
(VIII) is subsequently hydrolyzed by a basic hydrolysis reaction to produce the acid (IX);
step c):
the coupling conditions are chosen from 1-(3-dimethylaminopropyl)-3-ethylcarbodiimide hydrochloride (EDC)/1-hydroxybenzotriazole hydrate (HOBt), N,N'-Dicyclohexylcarbodiimide (DCC), N,N'-diisopropylcarbodiimide (DIC), O-(1H-Benzotriazol-1-yl)-N,N,N'N'-tetramethyl-uronium hexafluorophosphate, Trimethylacetyl chloride/i-Pr$_2$NEt, Trimethylacetyl chloride/Triethylamine, Trimethylacetyl chloride/N-methylmorpholine, Isobutyl chloroformate/triethylamine, Isobutyl chloroformate/N-methylmorpholine, Isobutyl chloroformate/i-Pr$_2$NEt, Ethylchloroformate/N-methylmorpholine, 2,4,6-trichlorobenzoly chloride/i-Pr$_2$NEt, 2,4,6-trichlorobenzoly chloride/triethylamine and 2,4,6-trichlorobenzoly chloride/Nomethylmorpholine.

5. The reaction according to claim 4 wherein:
step a):
the palladium catalyst is Pd(O—C(O)—CH$_3$)$_2$;
the ligand is 1,10-phenathroline;
step b):
(VIII) is subsequently hydrolyzed by a basic hydrolysis reaction with aqueous LiOH to produce the acid (IX);
step c):
the coupling conditions are EDC and HOBt.

* * * * *